(12) United States Patent
Chai et al.

(10) Patent No.: US 9,439,565 B1
(45) Date of Patent: Sep. 13, 2016

(54) WIRELESS VIEWING OF DIGITAL PATHOLOGY SPECIMENS

(71) Applicant: Dermatopathology Laboratory of Central States, Inc., Dayton, OH (US)

(72) Inventors: Gary Chai, Taipei (TW); Ben Chen, Taipei (TW); Sean Lin, Taipei (TW)

(73) Assignee: Dermatopathology Laboratory of Central States, Inc., Dayton, OH (US)

( * ) Notice: Subject to any disclaimer, the term of this patent is extended or adjusted under 35 U.S.C. 154(b) by 0 days.

(21) Appl. No.: 13/936,801

(22) Filed: Jul. 8, 2013

(51) Int. Cl.
*A61B 5/00* (2006.01)
*G06K 9/00* (2006.01)

(52) U.S. Cl.
CPC ...................................... *A61B 5/00* (2013.01)

(58) Field of Classification Search
None
See application file for complete search history.

(56) References Cited

U.S. PATENT DOCUMENTS

| | | | |
|---|---|---|---|
| 5,793,969 A | 8/1998 | Kamentsky et al. | |
| 6,101,265 A | 8/2000 | Bacus et al. | |
| 6,522,774 B1 * | 2/2003 | Bacus | G01N 15/1475 345/629 |
| 6,671,424 B1 * | 12/2003 | Skoll | G06T 1/60 382/305 |
| 6,763,140 B1 | 7/2004 | Skoll | |
| 7,113,625 B2 * | 9/2006 | Watson et al. | 382/133 |
| 7,738,688 B2 * | 6/2010 | Eichhorn | G02B 21/26 382/128 |
| 7,826,649 B2 | 11/2010 | Crandall et al. | |
| 7,856,131 B2 | 12/2010 | Bacus et al. | |
| 7,860,292 B2 | 12/2010 | Eichhorn et al. | |
| 8,010,555 B2 | 8/2011 | Eichhorn | |
| 8,199,358 B2 | 6/2012 | Eichhorn et al. | |
| 8,244,912 B2 | 8/2012 | Pace et al. | |
| 8,306,298 B2 | 11/2012 | Bacus et al. | |
| 8,775,424 B2 * | 7/2014 | Skaff | G06F 17/30265 382/305 |
| 2009/0210809 A1 * | 8/2009 | Bacus | G01N 1/312 715/764 |
| 2010/0067759 A1 * | 3/2010 | Zeineh | G06T 9/007 382/128 |
| 2011/0060766 A1 * | 3/2011 | Ehlke | G06F 3/0481 707/802 |
| 2012/0002892 A1 * | 1/2012 | Eichhorn | G02B 21/26 382/232 |
| 2012/0069049 A1 * | 3/2012 | Howe | G06T 7/0028 345/629 |
| 2012/0243753 A1 * | 9/2012 | Soenksen | G06T 7/0012 382/128 |
| 2012/0281931 A1 | 11/2012 | Eichhorn et al. | |
| 2012/0320094 A1 * | 12/2012 | Ruddle | G02B 21/367 345/660 |
| 2013/0034279 A1 | 2/2013 | Cosatto et al. | |

* cited by examiner

*Primary Examiner* — Matthew Bella
*Assistant Examiner* — Soo Shin
(74) *Attorney, Agent, or Firm* — Wood, Herron & Evans, LLP

(57) ABSTRACT

A digital microscope slide image tiling server 16 divides digital microscope slide image 24 into tiles 28. Each tile 28 is labeled with a magnification level and a location relative to the digital microscope slide image 24 that each tile 28 originated. A communications device 20 receives a pathologist selection 40 that designates a portion of a specimen to view at a different magnification. The communications device 20 provides the magnification level and location 44 to the digital microscope slide image tiling server 16. The digital microscope slide image tiling server 16 provides the tiles 38 labeled with the magnification level and location provided by the pathologist selection 40 to the communications device 20. The communications device 20 correlates the coordinate set associated with each tile 38 to the viewer interface of the communications device 20. The communications device 20 displays the tiles 38 via the viewer interface.

39 Claims, 6 Drawing Sheets

WIRELESS VIEWING OF DIGITAL PATHOLOGY SPECIMENS

FIELD OF THE INVENTION

The present invention relates to reviewing microscope slides of pathology specimens, and more specifically to wirelessly reviewing digital microscope slide images of pathology specimens.

BACKGROUND

Microscopes have long been used for centuries to view pathology specimens placed on microscope slides. The optical system of the microscope can be easily manipulated, and the slide moved around quickly, to allow the field of view to view large areas of the specimen at low magnification or to view smaller areas at greater magnification. This ease of use is important to those who use microscopes.

There has been a strong desire to use digital electronics for all sorts of purposes, including to replicate the behavior of a microscope in the digital world. For that purpose, it has been proposed to take digital images of pathology microscope slides and to store that image for later retrieval such as on a computer screen or other display. Such a so-called digital microscope is considered to present an advance, but current proposals are not sufficient.

Whatever portion of the slide image is to be viewed will typically fill the available screen viewing field, much like the field of view of the microscope. In order to assure that even the smallest portion can be viewed with sufficient clarity and detail, as if at maximum magnification, the entire slide must be imaged at a very high resolution sufficient to provide the necessary detail of every portion thereof. But in reality, it is typical for a pathologist or the like to first want to view the overall slide image, and then to "move" around the image at various levels of magnification to locate those areas that might be of concern.

With current proposals, every time a portion of the image is to be viewed, or even the overall image, a computer processing unit that may form part of a server must take all of that high resolution data for the selected image area, and re-compute a lower resolution version thereof sufficient to fill the viewing area. That process is very computer intensive. While the time involved can often be managed by today's powerful computers, it can still involve some amount of delay between the time the user "moves" the electronic version of the slide around on the screen and selects a magnification level. That delay frustrates the ability to use the digital microscope as a digital replication of traditional microscopes.

The problem becomes even more severe when one desires to view the specimen images on a remote, wireless communication device, such as smart phones, pads, notebooks, or the like. In that case, there is also the further drawback of the communication time involved in communicating the selection from the device to the server and the resend of the image data from the server, thus compounding the delays. Nor is it practical for the wireless communication device in most cases to receive all of the detailed data for maximum resolution of the entire slide image and then compute the data necessary for the selected image area and magnification.

SUMMARY OF THE INVENTION

The present invention provides an efficient and fast capability for viewing of pathology specimens with a digital microscope as a digital replication of a traditional microscope. To that end, and in accordance with the principles of the present invention, instead of relying on the server to re-compute each image, the server is provided a slide image at a high level of resolution representing a high level of magnification, and the image is divided into tiles that represent the image at various levels of lower resolutions representing selected levels of lower magnification and stored so that when a particular image area and magnification level are requested, the tiles associated therewith can be selected and the data for those tiles sent to the display. In that way, the field of view will be filled with data from the tiles corresponding to the selected image area and magnification, without the need to compute the data for that view. The foregoing also is of particular advantage in a wireless environment, for the wireless communication device need not store any more data than is required for the selected view, nor is there a compounded delay involved in waiting for the server to re-compute data for an image at the selected area and magnification.

As an example, a single image is taken at an extremely detailed and high resolution for maximum magnification. The single image is then divided into smaller portions, or tiles, representing the single image from extremely detailed and high resolution for maximum magnification to very low and limited detail for the lowest magnification level. For example, the quantity of tiles ranges from 1,000 tiles for low magnification and up to 10,000 tiles for maximum magnification. The data for the tiles is stored and tagged or labeled to identify its location and magnification level. When a slide is selected, the data for the 1,000 tiles may be sent to the communications device or screen. The user can then select an area and magnification level, which selection is then used by the server to select the appropriate tiles from the selected magnification level to essentially fill the viewing area of the screen, and that data is then sent to the screen or wireless device.

With the present invention, complex computations to re-compute images are reduced or eliminated, as that work was already done with the image levels that were stored at the server. The selection of an area for further viewing requires only that a location on the screen of the wireless device associated with the selection be provided to the server. The server then determines the tiles that are in the location of the selection and transmits only those tiles to the wireless device, thus reducing the amount of data exchanged and reducing delays from that process as well.

By virtue of the foregoing, there is thus provided an efficient and fast capability for viewing of pathology specimens with a digital microscope as a digital replication of a traditional microscope. These and other advantages shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments given below, serve to explain the principles of the present invention.

DETAILED DESCRIPTION OF THE DRAWINGS

Figure 1:
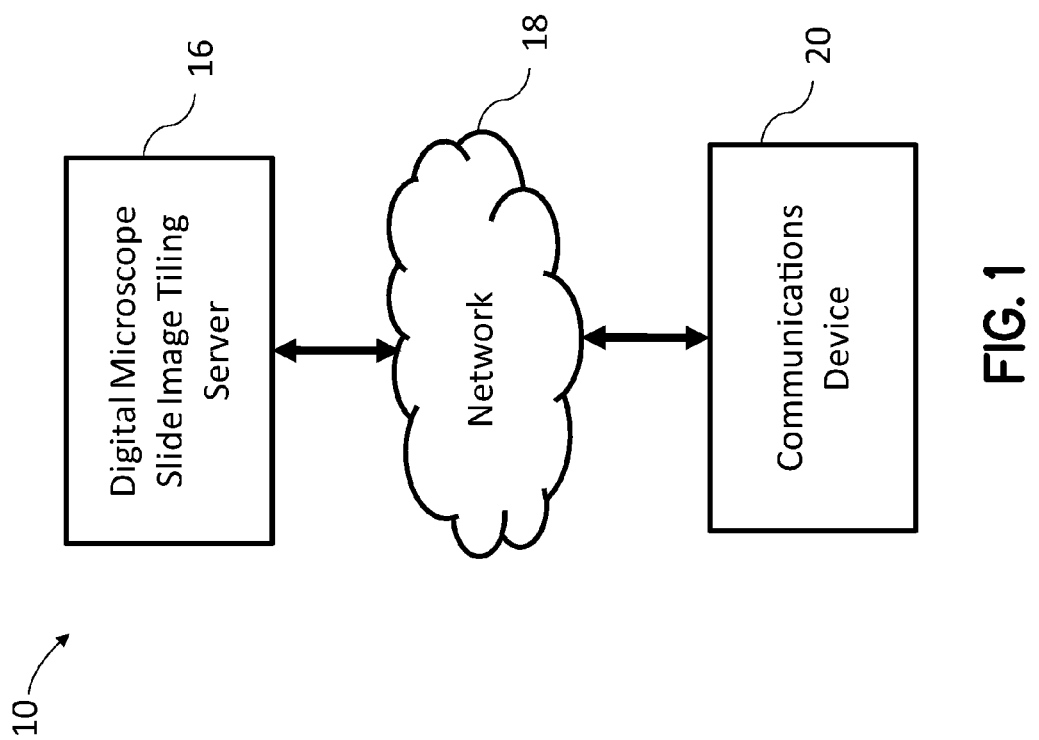
FIG. 1 is a schematic of an embodiment of a digital microscope slide image viewing system in accordance with the principles of the present invention.

With reference to FIG. 1, there are shown embodiments of a digital microscope slide image viewing system 10 of a digital microscope slide image 24 in accordance with the principles of the present invention. Generally speaking, one or more communications devices 20 connect to a digital microscope slide image tiling server 16 over a network 18. In embodiments, the digital microscope slide image tiling server 16 represents a cloud server, conventional web server or file transfer server and/or any other suitable server. The digital microscope slide image tiling server 16 includes at least one processor, at least one memory (which could take the form of RAM, cache, volatile and/or non-volatile, ROM, etc), and at least one network interface. Further the digital microscope slide image tiling server 16 may include any type of computer, computer system, or other programmable electronic processing or computing device having one or more microprocessors and/or microcontrollers and associated memory, IO, busses, graphical user or other interfaces adapted to form a user interface and may incorporate one or more user input devices (e.g., a keyboard, a mouse, a trackball, a joystick, a touchpad, and/or a microphone, among others) and a display (e.g., a CRT monitor, an LCD display panel, and/or a speaker, among others) with user input also possible being received via another computer or terminal. The digital microscope slide image tiling server 16 may be constituted by hardware with software and/or firmware programming and operating systems, and/or may be wholly or partially virtualized on a server. To that end, the digital microscope slide image tiling server 16 may be implemented using one or more networked computers, e.g., in a cluster or other distributing computing system, or may be implemented within a single computer or the like.

The communications device 20 is a communications device that includes at least one processor, at least one memory (which could take the form of RAM, cache, volatile and/or non-volatile, ROM, etc), and at least one network interface. For example, communications device 20 represents a smart phone, a smart tablet, a personal computer, handheld computer, a desktop computer, a personal digital assistant, and/or any other suitable communications device with a display. The communications device 20 may incorporate user input devices (e.g, a keyboard, a touch screen, a touchpad, a mouse, a trackball, a joystick, among others) and a display (e.g., a CRT monitor, and/or an LCD display panel, among others). The communications device 20 may be constituted with hardware with software and/or firmware programming and operating systems.

The network 18 includes one or more networks, such as the Internet. In some examples, the network 18 includes one or more wide area networks (WAN) or local area networks (LAN). The network 18 includes one or more network technologies such as Ethernet, Fast Ethernet, Gigabit Ethernet, a variant of IEEE 802.11 standard such as WiFi, and the like. Communication over the network 18 takes place using one or more network communication protocols including reliable streaming protocols such as transmission control protocol (TCP). These examples are illustrative and not intended to limit the present disclosure.

The communications device 20 is operated by a pathologist with the purpose to view digital microscope slide images that capture a specimen so that the pathologist can assess and diagnose the specimen from the communications device 20 rather than from a microscope located in a lab. However, the communications device 20 does not have the data bandwidth required to display the digital microscope slide images in a manner that is similar to using a microscope to view the actual slide of the specimen. As a result, the digital slide image tiling server 16 provides the appropriate tiles to the communications device 20 that when displayed by the communications device 20 to the pathologist depicts a portion of the specimen at a magnification level as selected by the pathologist. The digital slide image tiling server 16 continues to provide the appropriate tiles to the communications device 20 to enable the pathologist to view the digital microscope slide images of the specimen to adequately assess and diagnose the specimen using the communications device 20. The providing of tiles by the digital slide image tiling server 16 relieves the communications device 20 from exceeding the data bandwidth of the communications device 20 but yet provides the necessary performance required by the pathologist to adequately assess and diagnose the specimen.

Figure 2:
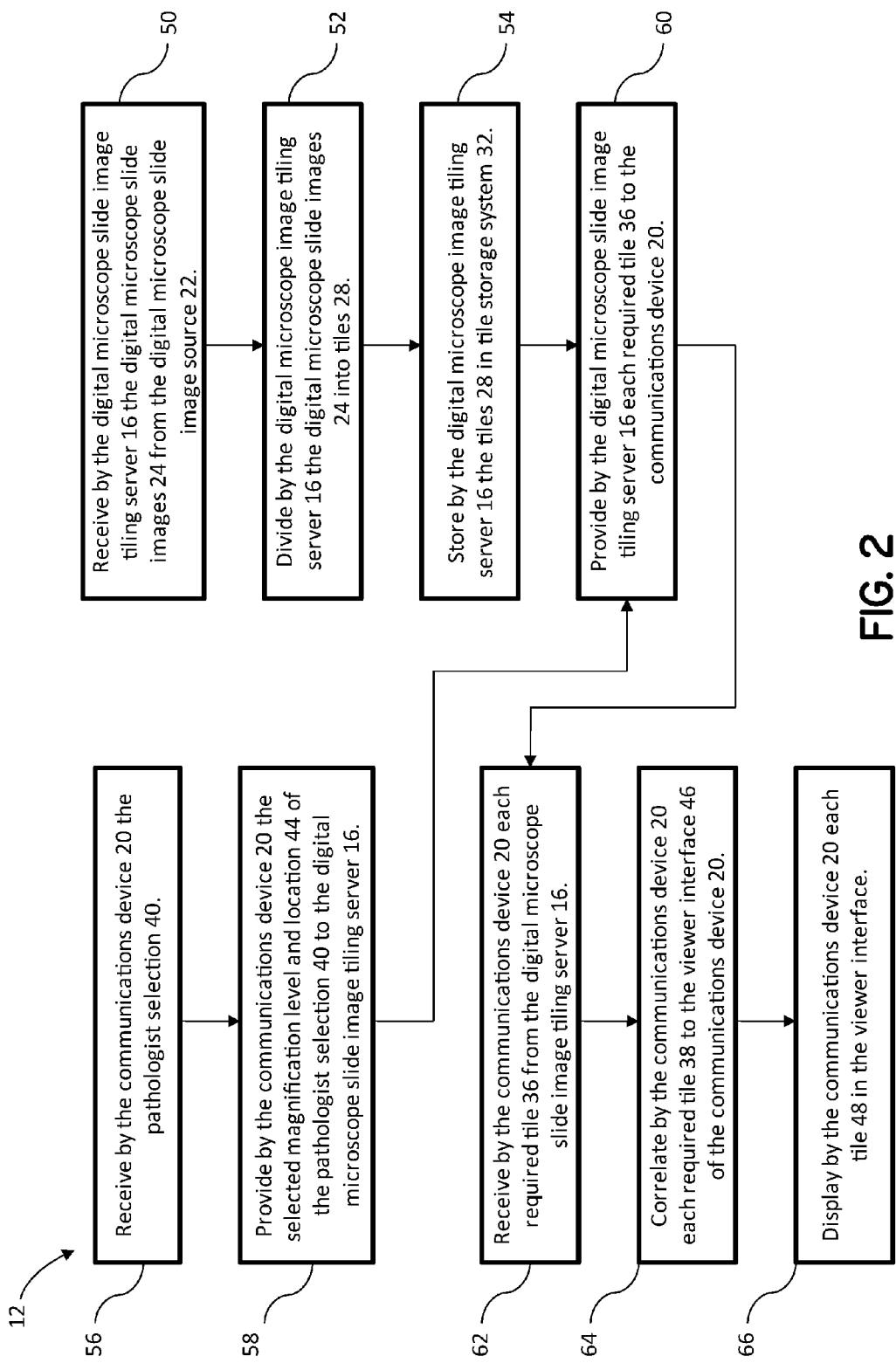
FIG. 2 is a flowchart of a digital microscope slide image viewing method in accordance with the principles of the present invention.
Figure 3:
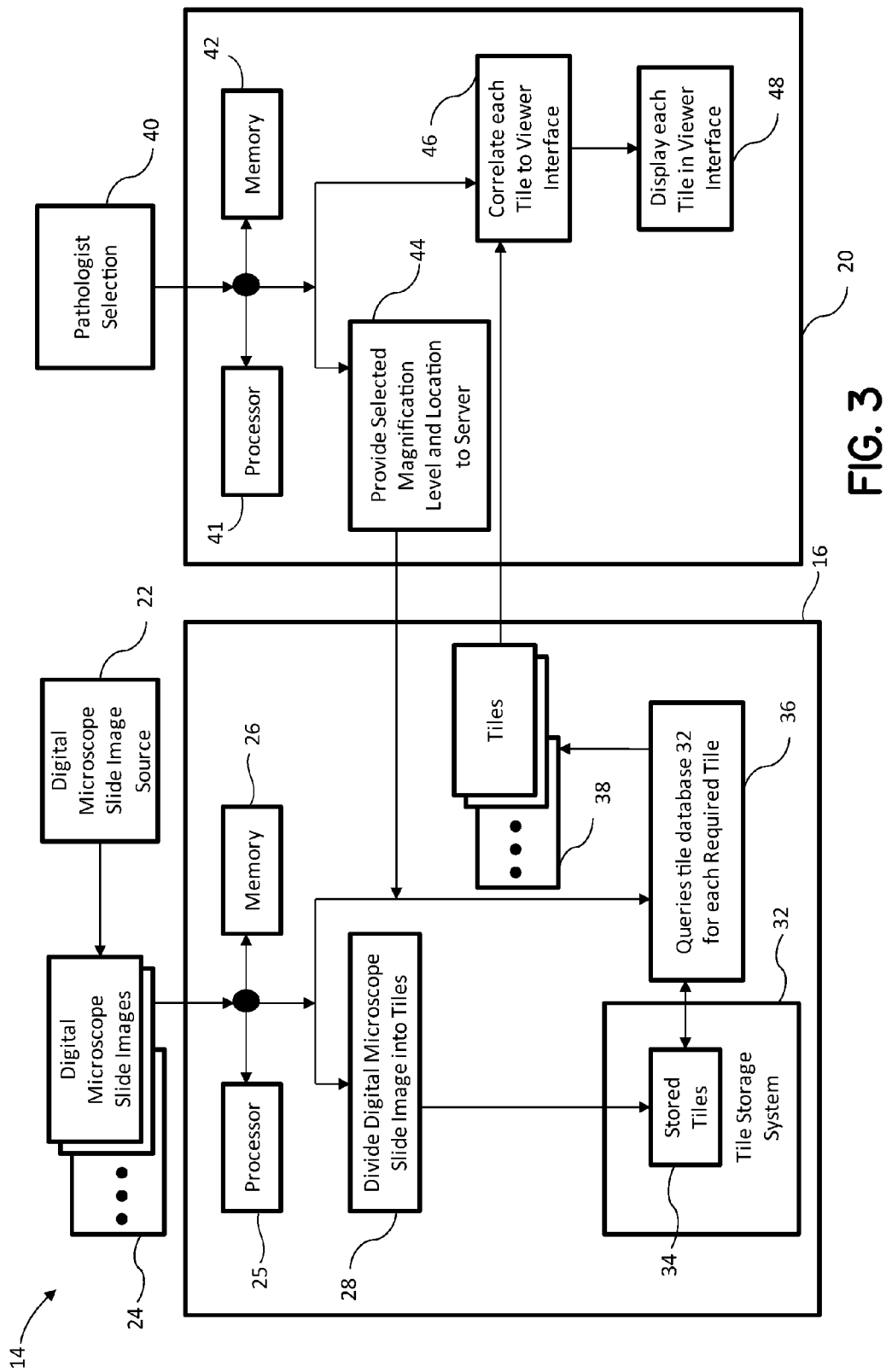
FIG. 3 is schematic of an embodiment of a digital microscope slide viewing system which may implement the method of FIG. 2.

With reference to FIGS. 2 and 3, there are shown embodiments of a method 12 and a digital microscope slide image viewing system 14 implementing the method 12, respectively, of viewing digital microscope slide images in accordance with the principles of the present invention. A digital microscope slide image source 22 provides digital microscope slide images 24, advantageously to a digital microscope slide image tiling server 16. The digital microscope slide image source 22 is a lab that generates microscope slides of specimens that are then captured by the digital microscope slide image source 22 into the digital microscope slide images 24. The digital microscope slide image source 22 is a lab that specializes in a common type of health risk such as skin disease. For example, the digital microscope slide image source 22 is a dermatopatholgy lab that places biopsies taken from patients onto microscope slides for assessment and diagnosis by a pathologist. The digital microscope slide image source 22 then generates digital microscope slide images 24 of each microscope slide of each skin specimen.

The digital microscope slide image source 22 captures the microscope slide of the specimen at a single magnification level that represents a high magnification level of the microscope in generating the digital microscope slide images 24. Thus, each digital microscope slide image 24 captured of the microscope slide of the specimen represents the specimen at a high magnification level. For example, digital microscope slide image source 22 captures digital microscope slide images 24 of the microscope slide of the specimen at single 50× magnification level. In the embodiment of the viewing of digital microscope slide images 24 of the present invention as exemplified by method 12, the digital microscope slide image tiling server 16 is programmed at step 50 to receive the digital microscope slide images 24 that have captured the specimen placed on the microscope slide at a high magnification level from the digital microscope slide image source 22. The digital microscope slide image tiling server 16 advantageously includes a processor 25 and a memory 26 which includes a data storage management system in the form of a computer program that when executing instructions on the processor 25, is used to read from and/or write accessible data structures of the memory 26.

In the embodiment of the viewing of the digital microscope slide images 24 of the present invention as exemplified by method 12, the digital microscope slide image tiling server 16 is programmed at step 52 to divide the digital microscope slide images 24 into tiles 38. As noted above, the digital microscope slide images 24 are large image files. The communications device 20 may not include sufficient processing capabilities to process the large image file for each digital microscope slide image 24 in a manner that enables the pathologist to maneuver throughout each digital microscope slide image 24 similar to that of using a microscope in the lab to view the actual microscope slide of the specimen. Thus, the digital microscope slide image tiling server 16 divides each digital microscope slide image 24 into tiles 38 upon receipt of each digital microscope slide image 24 from the digital microscope slide image source 22. The dividing of each digital microscope slide image 24 into tiles 38 by the digital microscope slide image tiling server 16 prevents the communications device 20 from occupying data bandwidth in processing each digital microscope slide image 24 for display to the pathologist and/or by having to divide each digital microscope slide image 24 into tiles 38 itself. For example, with reference to FIG. 4, an example digital microscope slide image 68 is divided into eight different tiles 70.*a* through 70.*h*.

Referring back to FIG. 3, typically, the pathologist that implements the microscope to assess and diagnose the microscope slides of specimens is able to change magnification levels of the microscope in order to zoom in and/or zoom out on portions of the specimen located on the microscope slide as the pathologist requires. For example, the pathologist is able to increase the magnification level of the microscope to view a portion of the specimen located on the microscope slide at a higher magnification so the pathologist is able to view the selected portion in greater detail. Conversely, the pathologist is able to decrease the magnification level of the microscope to view the portion of the specimen located on the microscope slide so the pathologist is able to view the selected portion relative to the rest of the specimen.

Similar to the microscope, the digital microscope slide image tiling server 16 divides the digital microscope slide image 24 captured at a high resolution into tiles 38 that represent the digital microscope slide image 24 ranging from the high resolution for the high magnification to the low resolution for the low magnification. Thus, the tiles 38 divided from the digital microscope slide image 24 represent the pathology specimen a different magnification levels. For example, the digital microscope slide image 24 is divided into tiles 38 that represent the microscope slide of the specimen at 10×, 20×, 30×, 40×, and 50× magnification levels. As a result, a first set of tiles 38 represent the microscope slide of the specimen at 10×, a second set of tiles 38 represent the microscope slide of the specimen at 20×, and so on.

The digital microscope slide image tiling server 16 selects a fixed tile size for each tile 38 that each digital microscope slide image 24 is divided. The digital microscope slide image tiling server 16 selects the fixed tile size for each tile 38 based on a resolution of the viewer interface of the communications device 20. The resolution of the viewer interface of the communications device 20 is fixed and is not going to vary. The viewer interface of the communications device 20 is capable of displaying a specific sized image in the viewer interface based on the resolution. The digital microscope slide image tiling server 16 determines the tile size for each tile 38 based on the size of the image that is to be displayed by the viewer interface of the communications device 20. After the selection of the tile size for each tile 38 by the digital microscope slide image tiling server 16, the tile size is fixed by the digital microscope slide image tiling server 16 so that each digital microscope slide image 24 is divided into tiles 38 that are of substantially equivalent size. For example, with reference to FIG. 4, each tile 70.*a* through 70.*h* has a fixed tile size defined by the dimensions d1 and d2.

Referring back to FIG. 3, the digital microscope slide image tiling server 16 determines the magnification level that for each tile 38. As noted above, each digital microscope slide image 24 captures the specimen at a high resolution and then the digital microscope slide image 24 is divided into tiles 38 at designated magnification levels ranging from a high resolution for maximum magnification to low resolution for low magnification. The digital microscope slide image tiling server 16 also determines the physical dimensions of each digital microscope slide image 24. For example, with reference to FIG. 4, the example digital microscope slide image 68 has a magnification level of 50×. The physical dimensions of the example digital microscope slide image 40 are designated by h1 and w1.

Referring back to FIG. 3, because the size for each tile 38 is fixed and the magnification level for each tile 38 and the physical dimensions of each digital microscope slide image 24 is known, the digital microscope slide image tiling server 16 is able to determine a quantity of tiles 38 to divide each digital microscope slide image 24 into. After the quantity of tiles 38 is determined, the digital microscope slide image tiling server 16 divides each digital microscope slide image 24 received by the digital microscope slide image source 22 into the determined quantity of tiles 38 for each designated magnification level. For example, with reference to FIG. 4, the size of each tile 70.*a* through 70.*h* is fixed with the dimensions of d1 and d2. The magnification level of the example digital microscope slide image 68 is 50× and the dimensions of the example microscope slide image 68 is h1 and w1. Based on the fixed tile size with dimensions d1 and d2, magnification level of 50× and the image size with dimensions h1 and w1, the example digital microscope slide image 68 is divided into the eight tiles 70.*a* through 70.*h* each with dimensions d1 and d2 for the magnification level of 50×.

Referring back to FIG. 3, the digital microscope slide image tiling server 16 labels each tile 38 with the magnification level of the microscope slide of the specimen that each tile 38 depicts. As noted above, each digital microscope slide image 24 captures the microscope slide of the specimen at a high resolution for a maximum magnification level and then divided into tiles 38 at specified magnification levels. Each tile 38 is then labeled by the digital microscope slide image tiling server 16 with the specified magnification level for each tile 38. For example, with reference to FIG. 4, the example digital microscope slide image 68 captured the microscope slide of the specimen at the magnification level of 50×. Thus, each tile 70.*a* through 70.*h* is labeled with the magnification level of 50×.

Referring back to FIG. 3, each tile 38 is also labeled by the digital microscope slide image tiling server 16 with a location of each tile 38 relative to the digital microscope slide image 24 that each tile 38 originated for each specified magnification level. The digital microscope slide image tiling server 16 associates a coordinate set to each tile 38 divided from a single digital microscope slide image 24 at a specified magnification level based on the location of each tile 38 relative to each other tile 38 divided from the single digital microscope slide image 24 at the specified magnification level. The digital microscope slide image tiling server 16 associates a (x, y) coordinate to each tile 38 divided from the single digital microscope slide image 24 at the specified magnification level where each (x, y) coordinate associated to each tile 38 is relative to each other tile 38 divided from the single digital microscope slide image 24 at the specified magnification level.

Figure 4:
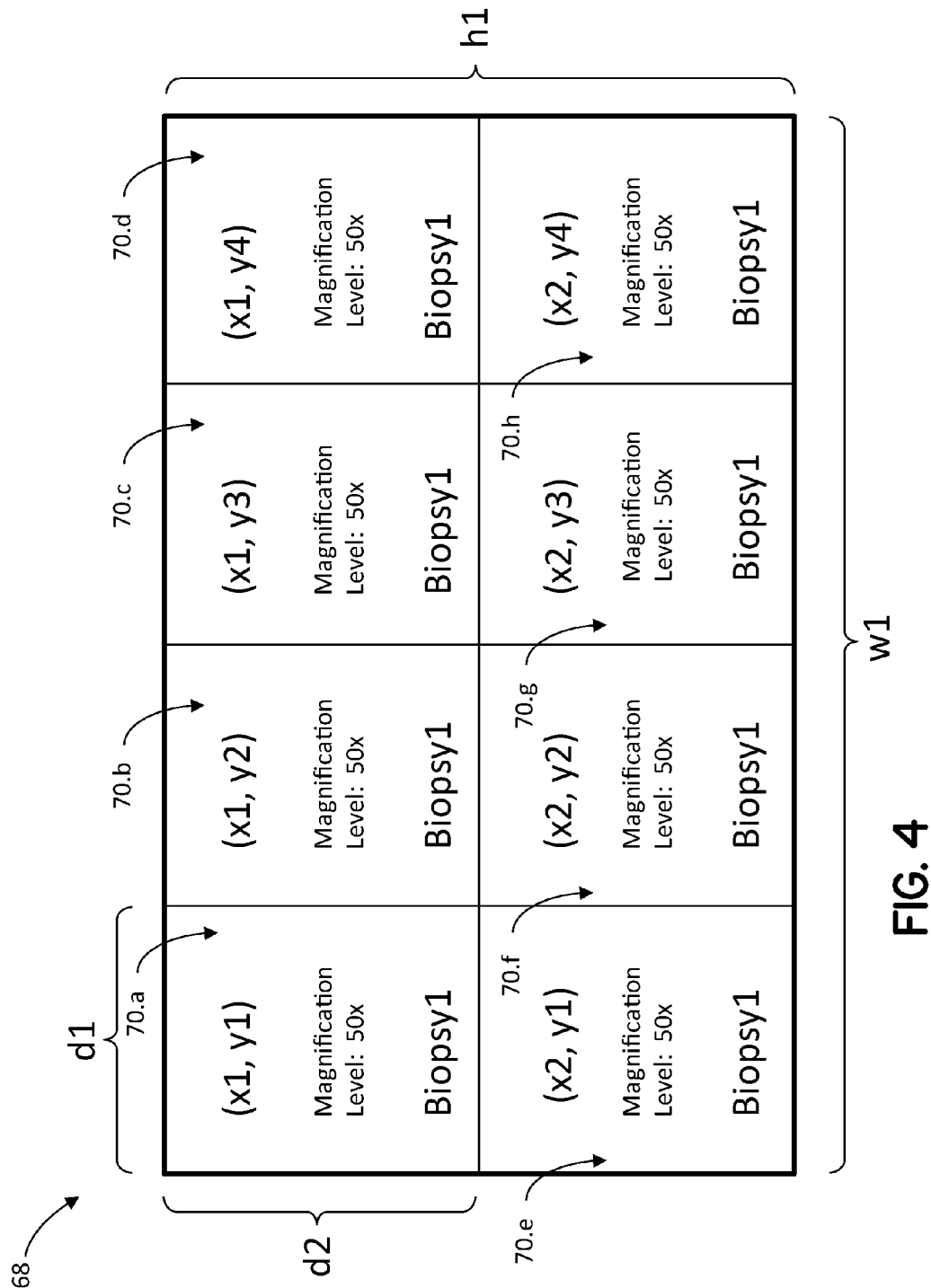
FIG. 4 is a schematic of an example digital microscope slide image divided into tiles in accordance with the principles of the present invention.

For example, with reference to FIG. 4, each tile 70.*a* through 70.*h* is associated with a (x, y) coordinate where each (x, y) coordinate for each tile 70.*a* through 70.*h* is relative to each other tile 70.*a* through 70.*h* divided from the example digital microscope slide image 68 at the specified magnification level of 50×. Tile 70.*a* is associated with the coordinate (x1, y1) based on the location of tile 70.*a* in the first x-axis position and the first y-axis position. Tile 70.*b* is associated with the coordinate (x1, y2) based on the location of tile 70.*b* in the first x-axis position and the second y-axis position. Based on the coordinate of (x1, y1) associated with the tile 70.*a* and the coordinate (x1, y2) associated with the tile 70.*b*, tile 70.*a* and tile 70.*b* are to be placed contingent to each other when the tiles 70.*a* through 70.*h* are reformulated by the communications device 20 and displayed to the pathologist.

Referring back to FIG. 3, the digital microscope slide image tiling server 16 labels each tile 38 with a name that includes the name of the specimen that each tile 38 depicts. As noted above, the digital microscope slide images 24 capture the microscope slide of a specimen at a high resolution for maximum magnification. Each microscope slide of the specimen includes a name of the specimen. As a result, each digital microscope slide image 24 also includes the name of the specimen that each digital microscope slide image 24 is captured. Each tile 38 also includes the name of the specimen depicted by the tile 38 based on the digital microscope slide image 24 that each tile 38 originated. For example, with reference to FIG. 4, the example digital microscope slide image 68 captures the specimen labeled Biopsy1. Thus, each tile 70.*a* through 70.*h* that originated from the example digital microscope slide image 68 is also labeled with Biopsy1.

With reference to FIGS. 2 and 3 in the embodiment of the viewing of the digital microscope slide images 24 of the present invention as exemplified by method 12, the digital microscope slide image tiling server 16 is programmed to store each tile 38 in a tile storage system 32 at step 54 until the communications device 20 requires the tiles 38 to be displayed by the communications device 20 to the pathologist. The stored tiles 34 may be stored in the tile storage system 32 of the system 14. The tile storage system 32 may be in the form of a storage system which cooperates in conventional fashion with the digital microscope image tiling server 16 in order to store and/or access the stored tiles 34. For example, each set of stored tiles 34 corresponding to each specified magnification level is stored in a corresponding folder in the tile storage system 32. In such an example, each of the stored tiles 34 for the magnification level of 40× are stored in a 40× folder in the tile storage system 32, each of the stored tiles for the magnification level of 30× are stored in a 30× folder, and so on. The tile storage system 32 may also be in the form of a relational database which cooperates in conventional fashion with the digital microscope image tiling server 16 in order to store and/or access the stored tiles 34. The tile storage system 32 may comprise one or more databases which may be configured in any database organization and/or structure, including, for example, relational databases, hierarchical databases, network databases, and/or combination thereof.

The tile storage system 32 may store the stored tiles 34 based on the label of each stored tile 34. As noted above, each stored tile 34 is labeled with a magnification level, a coordinate set, and a name of the specimen that each stored tile 34 depicts. As will be appreciated by those familiar with storage systems and server systems, the digital microscope slide image tiling server 16 may be programmed with various queries in uniform resource locator (URL) or other available programming languages, which are able to identify the stored tiles 34 stored in the tile storage system 32. The specific queries to adopt will be specific to the nature of the digital microscope slide image tiling server 16 but will follow the methodology of the invention as set out herein.

In the embodiment of the viewing of digital microscope slide images 24 of the present invention as exemplified by method 12, the communications device 20 is programmed at step 56 to receive a pathologist selection 40 from the pathologist. As noted above, the pathologist uses the communications device 20 to assess and diagnose the specimen by viewing the digital microscope slide images 24 that have captured the microscope slide of the specimen via the viewer interface of the communications device 20. The pathologist initially provides the selection 40 of the specimen that the pathologist desires to view via the communications device 20. The pathologist scrolls through the available specimens to view via the viewer interface of the communications device 20 and provides the selection 40 to the communications device 20 via the viewer interface.

After the pathologist initially selects the specimen to view and is viewing the specimen via the communications device 20, the pathologist provides the selection 40 of a location of the specimen relative to the viewer interface that the pathologist desires to view at a different magnification than the magnification that is currently displayed by the viewer interface of the communications device 20. The selection 40 provided by the pathologist designates the location of the specimen relative to the viewer interface that the pathologist desires to view at a different magnification level and also the magnification level that the pathologist desires to view the selected location of the specimen. For example, the pathologist desires to view the selected location of the specimen at a higher magnification level than the magnification level that the location of the specimen is currently displayed at by the viewer interface of the communications device 20. The pathologist touches the viewer interface of the communications device 20 at the location of the displayed specimen that the pathologist desires to view at the different magnification level and also inputs via the viewer interface of the communications device 20 the desired magnification level. The communications device 20 advantageously includes a processor 41 and a memory 42 which includes a computer program that when executing instructions on the processor 41, used to read from and/or write accessible data structures of the memory 42.

In step 58, the communications device 20 provides the selected magnification level and location 44 to the digital microscope slide image tiling server 16. The selected location 44 provided by the communications device 20 to the digital microscope slide image tiling server 16 is relative to a coordinate system for the viewer interface. The viewer interface includes an x-y coordinate system. The selected location 44 provided by the communications device 20 to the digital microscope slide image tiling server 16 includes a (x, y) coordinate relative to the x-y coordinate system of the viewer interface. Thus, the (x, y) coordinate set provided by the communications device 20 to the digital microscope slide image tiling server 16 is the (x, y) coordinate set where the pathologist touched the viewer interface in selecting the location of the specimen displayed by the viewer interface to view at a different magnification level.

At step 60, the digital microscope slide image tiling server 16 queries 36 the tile storage system 32 for the tiles 38 that are labeled with the designated magnification level and designated location as required by the communications device 20. The microscope slide image tiling server 16 queries 36 the tile storage system 32 for the tiles 38 that when displayed by the viewer interface of the communications device 20 display the location of the specimen at the magnification level as selected by the pathologist. As noted above, each stored tile 34 is labeled with the name of the specimen, the magnification level of the specimen, and the (x, y) coordinate set of each stored tile 34 relative to which portion of the specimen that the stored tile 34 depicts. Based on the specimen, the magnification level and the (x, y) coordinate set of the viewer interface selected by the pathologist, the digital microscope slide image tiling server 16 queries 36 the tile storage system 32 for each stored tile 34 labeled with the name of the specimen, the magnification level of the specimen, and the (x, y) coordinate set that corresponds to the selection of the pathologist.

After the pathologist provides the initial selection of which specimen to view via the viewer interface of the communications device 20, the digital microscope slide image tiling server 16 provides the tiles 38 that depict the specimen at a lowest magnification level. Thus, the initial viewing of the specimen by the pathologist is of the specimen at the lowest magnification level. The lowest magnification level of the specimen includes the stored tiles 34 that originated from the digital microscope slide image 24 that captured the microscope slide of the specimen at the lowest magnification level.

For the initial selection of the specimen by the pathologist, the digital microscope slide image tiling server 16 queries 36 the tile storage system 32 for each stored tile 34 labeled with the name of the specimen selected by the pathologist and also labeled with the lowest magnification level that the specimen was captured by the digital microscope slide images 24. The digital microscope slide image tiling server 16 provides the selected tiles 38 to the communications device 20 to display to the pathologist. The selected tiles 38 that depict the specimen at the lowest magnification level provide to the pathologist a substantially complete view of the specimen when displayed to the pathologist via the viewer interface of the communications device 20. As a result, the pathologist is able to view the substantially complete specimen when the selected tiles 38 depict the specimen at the lowest magnification level. The selected tiles 38 fill substantially the entire viewer interface when depicting the specimen at the lowest magnification level.

Figure 5A:
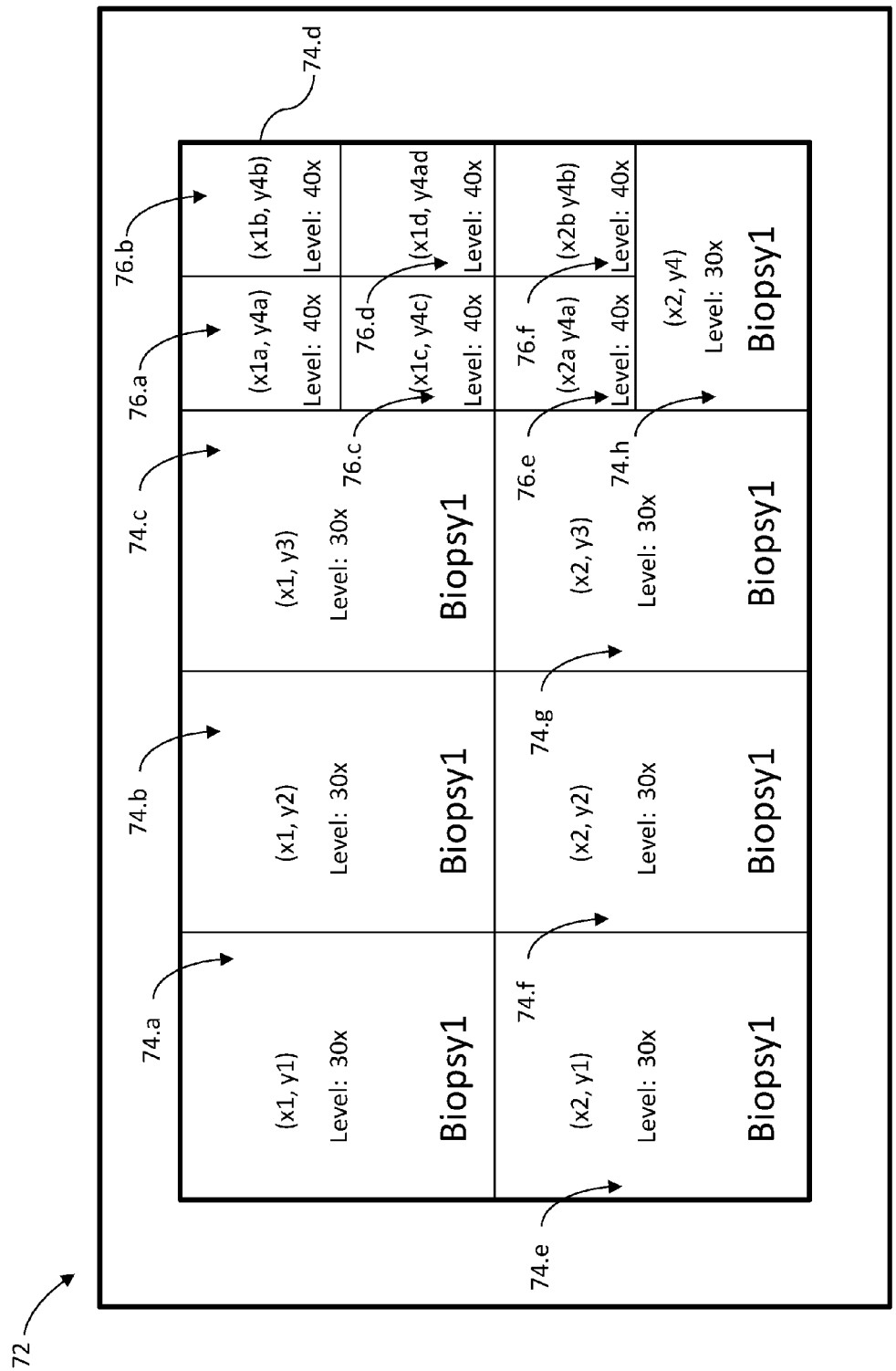
FIG. 5A is an example viewer interface of a communications device that is displaying tiles in accordance with the principles of the present invention.

For example, with reference to FIG. 5A, an example viewer interface 72 displays tiles 74.a through 74.h. Tiles 74.a through 74.h each depict the microscope slide of the specimen Biopsy1 at the magnification level of 30×. The magnification level of 30× is the lowest magnification level that the specimen Biopsy1 was captured. Thus, tiles 74.a through 74.h when displayed by the example viewer interface 72 depict a substantially complete image of the specimen Biopsy1 to the pathologist. The tiles 74.a through 74.h fill substantially the entire viewer interface when depicting the specimen Biopsy1 at the lowest magnification level of 30×.

Returning to FIG. 3, after the pathologist has been provided the tiles 38 that depict the specimen at the lowest magnification level, the pathologist then determines that to adequately assess and diagnose the specimen the pathologist requires to view a portion of the specimen at a higher magnification level than the magnification level previously displayed by the viewer interface of the communications device 20. The digital microscope slide image tiling server 16 queries 36 the tile storage system 32 for stored tiles 34 that are labeled with the higher magnification level required by the pathologist and also labeled with the location required by the pathologist. The digital microscope slide image tiling server 16 provides the selected tiles 38 to the viewer interface of the communications device 20 to display to the pathologist.

The pathologist generates the pathologist selection 40 by touching the viewer interface of the communications device 20 in the location of the viewer interface that depicts the portion of the specimen that the pathologist requires to view at the higher magnification level. The digital microscope slide image tiling server 16 queries the tile storage system 32 for the stored tiles that are labeled with the higher magnification level required by the pathologist and labeled with a (x, y) coordinate set that is within proximity of the location of the viewer interface that the pathologist touched when selecting the portion of the specimen to view at the higher magnification level. The digital microscope slide image tiling server 16 then provides the selected tiles 38 to the viewer interface of the communications device 20 to display to the pathologist. The selected tiles 38 fill substantially the entire viewer interface of the communications device when depicting the specimen at the higher magnification level.

Figure 5B:
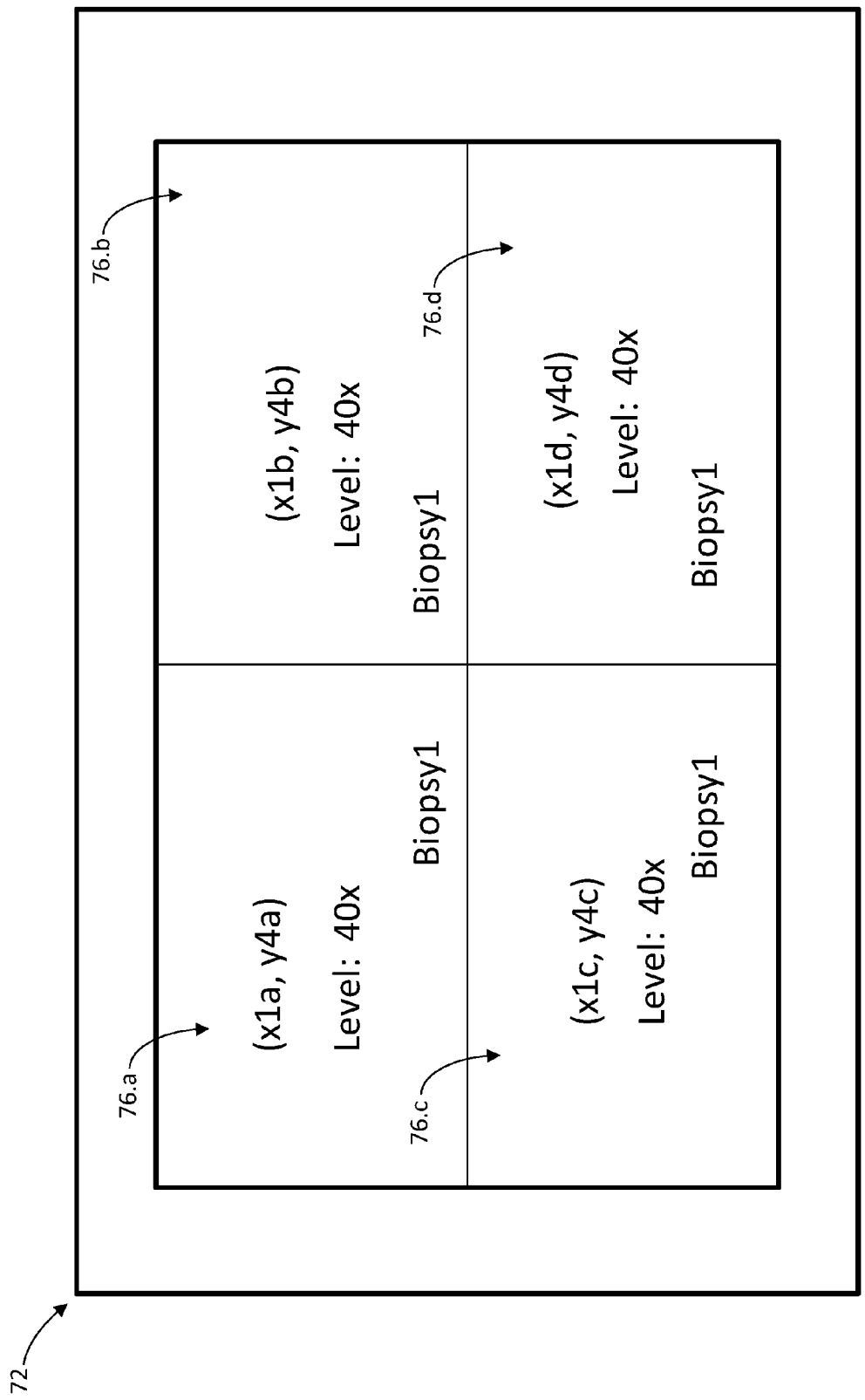
FIG. 5B is the example viewer interface of the communications device display tiles at a different magnification level than the example viewer interface depicted in FIG. 5A in accordance with the principles of the present invention.

For example, as shown in FIG. 5A, the example viewer interface 72 initially displays tiles 74.a through 74.h that each depicts the specimen Biopsy1 at the magnification level of 30×. The magnification level of 30× is the lowest magnification level of the specimen Biopsy1 resulting in initial display of tiles 74.a through 74.h to depict the specimen Biopsy1 to the pathologist at the lowest magnification level of 30×. After viewing the specimen Biopsy1 at the lowest magnification level of 30× as depicted by the tiles 74.a through 74.h, the pathologist requires to view the upper right hand corner of specimen Biopsy1 in further detail at a higher magnification level. The upper right hand corner of specimen Biopsy1 is depicted by the tile 74.d in FIG. 5A. The pathologist touches the example viewer interface 72 in the upper right hand corner of the specimen Biopsy1 depicted by the tile 74.d. The tiles 76.a through 76.d are the tiles that are within proximity of where the pathologist touched the example viewer interface 72 and are at the higher magnification level of 40×. Thus, as shown in FIG. 5B, the example viewer interface 72 no longer displays the specimen Biopsy1 at the magnification level of 30× as depicted by the tiles 74.a through 74.h. Rather, the example viewer interface 72 replaces the tiles 74.a through 74.h with the tiles 76.a through 76.*d* to display the upper right hand corner of specimen Biopsy1 at a higher magnification of 40× as depicted by the tiles 76.*a* through 76.*d*. The tiles 76.*a* through 76.*d* fill substantially the entire example viewer interface 72 when depicting the specimen Biopsy1 at the higher magnification level of 40×.

Returning to FIG. 3, the digital microscope slide image tiling server 16 determines a quantity of tiles required to fill the viewer interface of the communications device 20 based on the required magnification level and the portion of the specimen required by the pathologist to view at the required magnification level when the pathologist requires that the magnification level be changed. As noted above, the digital microscope slide image tiling server 16 previously divided each digital microscope slide image 24 into tiles 28 with each tile 28 having a fixed tile size. Thus, the tile size of each stored tile 34 at each magnification level is determined. Also, as noted above, the dimensions of the viewer interface has also been determined.

Based on the magnification level selected by the pathologist, the digital microscope slide image tiling server 16 confirms the tile size of the stored tiles 34 labeled with the selected magnification level. Based on the tile size for the selected magnification level, the dimensions of the viewer interface, and the (x, y) coordinate location on the viewer interface that the pathologist touched, the digital microscope slide image tiling server 16 determines the quantity of tiles required to fill the viewer interface to provide the pathologist a view of the selected portion of the specimen at the selected magnification level. For example, as shown in FIG. 5A, the pathologist touches the upper right hand corner of the example viewer interface 72 represented by tile 74.*d* to view that the portion of the specimen at a higher magnification of 40×. As shown in FIG. 5B, the example viewing interface 72 displays four tiles 76.*a* through 76.*d* at the selected magnification level 40× to display to the pathologist the upper right hand corner of the specimen in greater detail.

Returning to FIG. 3, after the digital microscope slide image tiling server 16 determines the quantity of tiles 38 to provide to the communications device 18, the digital microscope slide image tiling server 16 queries the tile storage system 32 for each stored tile 34 with a coordinate set within proximity of the location of where the pathologist touched the viewer interface until the quantity of tiles required to fill the viewer interface is substantially fulfilled. The digital microscope slide image tiling server 16 selects a first stored tile 34 from the tile storage system 32 with the (x, y) coordinate set that is substantially closest to the (x, y) coordinate location on the viewer interface that the pathologist touched in selecting the portion of the specimen to view at the higher magnification level. The digital microscope slide image tiling server 16 then selects a second stored tile 34 from the tile storage system 32 that is previously unselected with the (x, y) coordinate set that is substantially closest to the (x, y) coordinate location on the viewer interface from the remaining unselected stored tiles 34 stored in the tile storage system 32. The digital microscope slide image tiling server 16 continues to select each stored tile 34 from the tile storage system 32 that is previously unselected with the (x, y) coordinate set that is substantially closest to the (x, y) coordinate location until the quantity of tiles 38 required to substantially fill the viewer interface have been selected from the tile storage system 32.

For example, as shown in FIG. 5A, the pathologist touches the upper right hand corner of the example viewer interface 72 depicted by the tile 74.*d* to view the selected portion of the specimen at the magnification level of 40× rather than the current magnification level of 30× currently displayed by the example viewer interface 72. Based on the (x1, y4) coordinate set that is associated with the pathologist's selection of the upper right hand corner of the viewer interface depicted by the tile 74.*d*, a total of four tiles is determined to display the upper right hand corner of the viewer interface depicted by the tile 74.*d* at the magnification level of 40×. As shown in FIG. 5B, the tile 76.*a* with the coordinate set (x1a, y4a) is selected as the tile substantially closest to the pathologist's selection of the coordinate set (x1, y4). The tile 76.*b* with the coordinate set (x1b, y4b) is selected as the previously unselected tile that is substantially closest to the pathologist's selection of the coordinate set (x1, y4) remaining from the unselected tiles. The tile 76.*c* with the coordinate set (x1c, y4c) is then selected as the previously unselected tile that is substantially closest to the pathologist's selection of the coordinate set (x1, y4) remaining from the unselected tiles. The tile 76.*d* with the coordinate set (x1d, y4d) is then selected as the previously unselected tile that is substantially closest to the pathologist's selection of the coordinate set (x1d, y4d) remaining from the unselected tiles. After the tile 76.*d* is selected, the quantity of four tiles required to substantially fill the example viewer interface 72 with tiles to adequately display the upper right hand corner of the example viewer interface 72 at the magnification level of 40× has been fulfilled. The tiles 76.*a* through 76.*d* are then displayed by the example viewer interface 72 to the pathologist.

Returning to FIG. 3, after the digital microscope slide image tiling server 16 provides tiles 38 to the communications device 20 that depict the selected portion of the specimen at the selected magnification level to the pathologist, the digital microscope slide image tiling server 16 anticipates that the pathologist is going to pan through the image currently displayed to the pathologist. The digital microscope slide image tiling server 16 anticipates that the pathologist is going to pan through the current image displayed to the pathologist and begins to pull stored tiles 34 that are located within proximity of the tiles 38 currently displayed to the pathologist. The digital microscope slide image tiling server 16 pulls stored tiles 34 that are labeled with (x, y) coordinate sets that are within proximity of the (x, y) coordinate sets for the tiles 38 currently displayed to the pathologist and also labeled with the same magnification level as the magnification level of the tiles 38 currently displayed to the pathologist. Thus, the stored tiles 34 with (x, y) coordinate sets within proximity of the (x, y) coordinate sets associated with the tiles 38 currently displayed to the pathologist are pulled and ready to be displayed to the pathologist if the pathologist begins to pan through the specimen.

For example, as shown in FIG. 5A, the pathologist selects to view the upper right hand portion of the specimen Biopsy1 displayed by the example viewer interface 72 as depicted by the tile 74.*d* at the higher magnification level of 40×. As shown in FIG. 5B, the example viewer interface 72 displays the tiles 76.*a* through 76.*d* that display the upper right hand portion of the specimen Biopsy1 at the higher magnification level of 40×. In anticipation that the pathologist is going to pan through the portion of the specimen Biopsy1 currently displayed by the viewer interface 72 depicted by the tiles 76.*a* through 76.*d* at the magnification level of 40×, the viewer interface 72 as shown in FIG. 5A pulls tiles 76.*e* and 76.*f*. The tiles 76.*e* and 76.*f* depict the specimen Biopsy1 at the magnification level of 40×. However, the tiles 76.*e* and 76.*f* are labeled with the coordinate set of (x2a, y4a) and (x2b, y4b), respectively. The coordinate set of (x2a, y4a) for tile 76.*e* and (x2b, y4b) for tile 76.*f* are within proximity of the coordinate set of (x1c, y4) for the tile 76.*c* and the coordinate set of (x1d, y4d) for the tile 76.*d*. Tiles 76.*c* and 76.*d* are currently displayed by the example viewer interface 72 to the pathologist. However, the example viewer interface 72 has tiles 76.*e* and 76.*f* pulled and ready to display to the pathologist if the pathologist were to pan down from the upper right hand corner of the specimen Biopsy1 depicted by the tile 74.*d* to the lower right hand corner of the specimen Biopsy1 depicted by the tile 74.*h*.

Returning to FIG. 3, with the appropriate tiles 38 queried from the tile storage system 32 by the digital microscope slide image tiling server 16 to substantially fill the viewer interface of the communications device 20, at step 62, the communications device receives the tiles 38 from the digital microscope slide image tiling server 16. Each tile 38 received by the communications device 20 is labeled with the magnification level and the tile location that is associated with the selection of the pathologist to view the selected portion of the specimen at the selected magnification level. As noted above, each tile 38 is labeled with the (x, y) coordinate set that is within proximity of the (x, y) location of the viewer interface touched by the pathologist that is required to substantially fill the viewer interface with the tiles 38.

The tiles 38 received by the communications device 20 are each labeled with the (x, y) coordinate set. As noted above, the (x, y) coordinate set for each tile 38 is relative to each other tile 38 that originated from the same digital microscope slide image 24. However, each tile 38 is to be properly displayed in the viewer interface of the communications device 20. To that end, after each tile 38 is received, the communications device 20 correlates the tile location for each received tile 38 to the location on the viewer interface at step 64. As noted above, the viewer interface of the communications device 20 also is based on a coordinate system that includes an x-axis and a y-axis. Thus, each portion of the viewer interface is associated with an (x, y) coordinate. The communications device 20 correlates the (x, y) coordinate set associated with each received tile 38 to the corresponding (x, y) coordinate set associated with the viewer interface. As a result, the communications device maps each received tile 38 to the viewer interface based on the (x, y) coordinate set associated with each received tile 38 and the corresponding (x, y) coordinate set associated with the viewer interface.

For example, as shown in FIG. 4, each tile 70.*a* through 70.*h* divided from the example digital microscope slide image 68 is associated with a (x, y) coordinate set. As shown in FIG. 5A, the example viewing interface 72 is divided into portions that are each associated with a (x, y) coordinate set. Each tile 70.*a* through 70.*h* divided from the example digital microscope slide image 68 as shown in FIG. 4 is mapped to the corresponding portion of the example viewing interface 72 based on the (x, y) coordinate set associated with each tile 70.*a* through 70.*h* and the (x, y) coordinate set of each portion of the example viewing interface 72. For example, tile 70.*a* as shown in FIG. 4 associated with the coordinate set of (x1, y1) is mapped to the portion of the example viewing interface 72 associated with the coordinate set of (x1, y1) as shown in FIG. 5A. Thus, each tile 70.*a* through 70.*h* is properly displayed by the example viewing interface 72.

After the communications device 20 correlates the (x, y) coordinate set associated with each received tile 38 to the (x, y) coordinate set associated with the viewer interface, then at step 66, the communications device 20 displays each tile 48 in the viewer interface based on the correlation of tile 48 to the viewer interface. The display of each tile 48 in the viewer interface properly displays the selected portion of the specimen at the selected magnification level as selected by the pathologist. The display of each tile 48 is done so that the pathologist can properly assess and diagnose the portion of the specimen displayed by the viewer interface similar to using an actual microscope to assess and diagnose the specimen in the lab. As a result, the display of the specimen by the viewer interface to the pathologist enables the pathologist to properly assess and diagnose the specimen remotely from the communications device 20 rather than being stationed in the lab.

After the portion of the specimen is displayed to the pathologist, the pathologist may adjust the resolution of the displayed tiles 48 displayed via the pathologist within a threshold without having to receive additional tiles 38 from the digital microscope slide image tiling server 16. The communications device 20 provides the pathologist the capability to adjust the resolution of the displayed tiles 48 within a threshold before crossing into a different magnification level which would require additional tiles 38 labeled with the different magnification level to properly display the selected portion of the specimen to the pathologist. The communications device 20 provides the pathologist to zoom in and/or zoom out in adjusting the resolution of the displayed tiles 48 in small increments before having to cross the threshold requiring additional tiles 38 be provided to display the selected portion of the specimen at a different magnification level than what is currently being displayed.

For example, as shown in FIG. 5A, the example viewer interface 72 displays the specimen Biopsy1 at the magnification level of 30×. The example viewer interface 72 enables the pathologist to adjust the resolution of tile 76.*d* in small increments to zoom in on tile 76.*d* without having to cross into the magnification level of 40×. However, after the pathologist adjusts the resolution of tile 76.*d* beyond the threshold which changes the magnification level to 40×, then the example viewer interface 72 replaces tiles 74.*a* through 74.*h* with tiles 76.*a* through 76.*d* as shown in FIG. 5B to display the selected portion of the specimen Biopsy1 at the magnification level of 40×.

The digital microscope slide image tiling server 16, the communications device 20, the digital microscope slide image source 22 and the tile storage system 32 share resources via network 18. For example, the digital microscope slice image tiling server 16 retrieves stored tiles from the tile storage system 32. The communications device 20 also provides to the tile storage system 32 the selected magnification level and the selected location of the specimen relative to the viewer interface for tiles 48 that are to be displayed by the viewer interface. The digital microscope side image source 22 provides additional digital microscope slide images 24 that are divided into tiles 34 that are stored in the tile storage system 32. Based on the cloud computing configuration, the interaction between the digital microscope slide image tiling server 16, the communications device 20, the digital microscope slide image source 22 and the tile storage system 32 may not be limited to a single computing device. For example, a plurality of computing devices may update the tile storage system 32 with tiles from other digital microscope slide images 24 captured by other digital microscope slide image sources 22.

In use, with the method 12 and digital microscope slide image viewing system 14, the digital microscope slide image tiling server 16 receives the digital microscope slide images 24 that capture the specimen at different magnification levels from the digital microscope slide image source 22. The digital microscope image tiling server 16 divides the digital microscope slide images 24 into tiles 38. The digital microscope image tiling server 16 stores each tile 34. Each stored tile 34 is labeled with the magnification level that each stored tile 34 depicts of the specimen based on the magnification level of the digital microscope slide image 24 that each stored tile 34 originated. Each stored tile 34 is also labeled with the (x, y) coordinate set that depicts the location of each stored tile 34 relative to each other stored tile 34 that originated from the same digital microscope slide image 24.

Further in use, with the method 12 and digital microscope slide image viewing system 14, the communications device 20 receives the selection 40 from the pathologist implementing the communications device 20 that depicts a location of the specimen relative to the viewer interface of the communications device 20 to be displayed at a selected magnification level. The communications device 20 provides the selected magnification and the selected location 44 of the specimen that is to be displayed by the viewer interface. The digital microscope slide image tiling server 16 provides each tile 38 from the tile storage system 32 to the communications device 20 that is labeled with the selected magnification level and the (x, y) coordinate set relative to the selected location as provided by the pathologist selection 40. The communications device 20 correlates 46 the (x, y) coordinate set of each received tile 38 to the (x, y) coordinate set of the viewer interface. The communications device 20 displays each tile 48 based on the correlation of the (x, y) coordinate set of each displayed tile 48 to the (x, y) coordinate set of the viewer interface.

It will be seen from the above that the digital microscope slide image viewing method 12 provides the pathologist the ability to adequately assess and diagnose digital microscope slide images 24 of the microscope slide of a specimen in a manner similar to that of using an actual microscope to assess and diagnose the actual microscope slide of the specimen. The dividing of the microscope slide images 24 into tiles 38 and then the storing of the tiles 34 in the tile storage system 32 relieves the data bandwidth of the communications device 20 from having to process each microscope slide image 24 based on the needs of the pathologist. Rather, the communications device 20 displays the necessary tiles 48 to the pathologist based on the selection 40 of the pathologist to view a portion of the specimen at a magnification level. For each selection 40 by the pathologist, the digital microscope slide image tiling server 16 provides the appropriate tiles 38 that depict the portion of the specimen at the magnification level selected by the pathologist. There is thus provided a digital microscope slide image viewing experience that provides adequate performance to the communications device to provide an experience to the pathologist in assessing and diagnosing the specimen via the communications device that is similar that of using an actual microscope to view the microscope slide for the specimen.

The digital microscope slide image viewing method 12, or at least portions thereof of the present invention is implemented on a computer processing unit, such as the digital microscope image tiling server 16 and/or the communications device 20, to execute instructions to perform operations to provide the digital microscope slide image viewing method 12 to pathologists implementing the communications device 20 to view tiles 38 depicting the digital microscope slide images 24. The various instructions may be included as part of a program product (not shown) such as a disc, memory stick, flash drive, downloadable object, or the like as will be understood by the skilled artisan. Furthermore, it will be appreciated that implementation of the herein-described functionality in program code would be well within the abilities of one of ordinary skill in the art having the benefit of the instant disclosure.

While the present invention has been illustrated by description of embodiments thereof and while the embodiments have been described in considerable detail, it is not intended to restrict or in any way limit the scope of the appended claims to such detail. Additional advantages and modifications will readily appear to those skilled in the art. And while an embodiment described may include a particular feature, structure, or characteristic, every embodiment of the invention may not necessarily include the particular feature, structure, or characteristic. By way of example, the method of the present invention could include steps that include providing tiles that depict the selected portion of the specimen to a lower magnification level than the magnification level currently displayed to the pathologist. Also, while a (x, y) coordinate system is described for both the tiles relative to the digital microscope slide image that each tile originated and the viewer interface of the communications device, it will be appreciated that different coordinate systems may be implemented. Further, the coordinate system implemented for the tiles may be different than the coordinate system implemented for the view interface. In such an example, the communications device would correlate the different coordinate systems. The invention in its broader aspects is therefore not limited to the specific details, representative apparatus and methods shown and described. Accordingly, departures may be made from such details without departing from the scope or spirit of applicant's general inventive concept.

Having described the invention, what is claimed is:

1. A viewing method for digital microscope slide images of a specimen, comprises a server to:
   receive, at the server, a single digital microscope slide image that captures the specimen at a high magnification level;
   divide the single digital microscope slide image at the high magnification level into a plurality of tiles at a plurality of magnification levels by automatically adjusting the high magnification level of the single digital microscope slide image initially captured of the specimen to the plurality of magnification levels, with one or more of the magnification levels being at a lower magnification level than the initial high magnification level;
   generate the plurality of tiles at the plurality of magnification levels from the single digital microscope slide image at the high magnification level initially captured of the specimen, wherein each of the tiles with one or more of the magnification levels being at a lower magnification level than the initial magnification level is derived from the single digital microscope slide image at the high magnification level;
   store each tile derived from the single digital microscope slide image at the high magnification level in a tile storage system, wherein each tile is labeled with a magnification level of each tile and a location of each tile relative to the magnification level of each digital microscope slide image that each tile originated that correlates to a viewer interface of a communications device; and
   provide each tile from the tile storage system to the communications device that is labeled with a designated magnification level and a designated location as required by the communications device.

2. The method of claim 1, wherein each tile is labeled with a location that includes a coordinate set that correlates to a location of each tile relative to the digital microscope slide image that each tile originated from to a coordinate system for the viewer interface of the communications device.

3. The method of claim 1, wherein dividing the single digital microscope slide image includes:
selecting a fixed tile size for each tile that the single digital microscope image is divided into based on a resolution of the viewer interface of the communications device;
determining the magnification level of each tile and physical dimensions of the single digital microscope slide image; and
dividing the single digital microscope slide image into the plurality of tiles based on the selected fixed tile size, the determined magnification level of each tile, and the determined physical dimensions of the single digital microscope slide image.

4. The method of claim 3, further comprising:
associating a coordinate set to each tile for a designated magnification level divided from a single digital microscope slide image based on a location of each tile relative to each other tile divided from the single digital microscope image at the designated magnification level; and
correlating each coordinate set associated with each tile to the coordinate system of the viewer interface of the communications device.

5. The method of claim 4, wherein the coordinate set includes an x-axis coordinate and a y-axis coordinate.

6. The method of claim 4, wherein the coordinate system of the viewer interface of the communications device includes an x-axis and a y-axis.

7. The method of claim 4, wherein the providing of each tile from the tile storage system to the communications device includes positioning each tile in the viewer interface based on each coordinate set associated with each tile that is correlated to the coordinate system of the viewer interface.

8. The method of claim 1, wherein the labeling of each tile includes a name of the specimen that is depicted by each tile.

9. The method of claim 1, wherein the providing of each tile from the tile storage system to the communications device includes initially providing a plurality of lowest resolution tiles to the communications device when the specimen is initially provided to the communications device, wherein the plurality of lowest resolution tiles includes each tile stored in the tile storage system with a lowest magnification level of the tiles stored in the tile storage system.

10. The method of claim 9, wherein the plurality of lowest resolution tiles provides a substantially complete image of the specimen to the communications device.

11. The method of claim 10, wherein the providing of each tile from the tile storage system to the viewer interface includes providing a plurality of higher resolution tiles to the communications device when required by the communications device to provide a portion of the specimen at a higher magnification than what is currently provided to the communications device.

12. The method of claim 11, wherein the plurality of higher resolution tiles provides less than the substantially complete image of the specimen to the communications device.

13. The method of claim 10, wherein the providing each tile from the tile storage system to the communications device includes:
querying the tile storage system for each tile that is labeled with the required magnification level and the coordinate set that is adjacent to the portion of the specimen required by the communications device that is at the higher magnification than what is currently provided to the communications device; and
providing each tile from the tile storage system to the communications device that is labeled with the selected magnification level and the coordinate set that is adjacent to the portion of the specimen required by the communications device that is at the higher magnification than what is currently provided to the communications device.

14. The method of claim 10, wherein the providing each tile from the tile storage system to the communications device includes:
determining a quantity of tiles required to fill the viewer interface of the communications device based on the required magnification level and the portion of the specimen required by the communications device that is at the higher magnification than what is currently provided to the communications device.

15. The method of claim 14, further comprising:
determining a required coordinate set associated with the portion of the specimen required by the communications device that correlates to the coordinate system of the viewer interface; and
querying the tile storage system for each tile with a coordinate set that is adjacent to the required coordinate set associated with the portion of the specimen required by the communications device and is at the required magnification level until the quantity of tiles required to fill the viewer interface is substantially fulfilled.

16. The method of claim 15, wherein querying the tile storage system for each tile includes:
selecting a tile stored in the tile storage system with a coordinate set that is a minimum difference from the selected coordinate set associated with the portion of the specimen required by the communications device;
selecting a previously unselected tile stored in the tile storage system with the coordinate set that is a minimum difference from the selected coordinate set associated with the portion of the specimen required by the communications device; and
continuing to select each previously unselected tile stored in the tile storage system with the coordinate set that is a minimum difference from the selected coordinate set associated with the portion of the specimen required by the communications device until the quantity of tiles required to fill the viewer interface is substantially fulfilled.

17. The method of claim 1, wherein the storing of each tile in the tile storage system includes storing tiles that capture the specimen at the plurality of magnification levels.

18. The method of claim 1, wherein the dividing of the single digital microscope slide image into a plurality of tiles by the server prevents the communications device from occupying bandwidth of the communications device to divide the single digital microscope slide image into the plurality of tiles.

19. The method of claim 1, wherein the storing each tile in the tile storage system includes storing each tile in a cloud computing environment.

20. A viewing method for digital microscope slide images of a specimen, comprises a communications device configured to:
receive, at the communications device, a selection from a user of the communications device that selects a location of the specimen relative to a viewer interface of the communications device to be displayed at a selected magnification level by the viewer interface;

provide the selected magnification level and the location of the specimen relative to the viewer interface that is to be displayed at the selected magnification level to a server that stores a plurality of tiles that a plurality of digital microscope slide images that depict the specimen is divided into;

receive each tile provided by the server that is labeled with the selected magnification level and a tile location that is associated with the selection of the user;

correlate the tile location of each tile received from the server to a location of the viewer interface;

display each tile provided by the server that is labeled with the selected magnification level and the tile location that is associated with the selection of the user based on the correlation of each tile location to each corresponding location of the viewer interface;

receive an additional selection from the user that selects the location of the specimen relative to the viewer interface that is to be displayed at a higher magnification level than what is currently displayed by the viewer interface;

display each tile that is labeled with the higher magnification selected by the user and the coordinate set that is adjacent to the location selected by the user;

request from the server each tile at the higher magnification level that is adjacent to each tile currently displayed;

store each tile at the higher magnification level that is adjacent to each tile currently displayed to display when the user pans through the specimen that is currently displayed by the viewer interface; and display an anticipated tile at the higher magnification level stored by the communications device when the user pans from a currently displayed tile to a location that is adjacent to the currently displayed tile without having to request the anticipated tile from the server after the user pans from the currently displayed tile.

21. The method of claim 20, wherein the providing the location of the specimen relative to the viewer interface includes providing the location of the specimen relative to a coordinate system for the viewer interface.

22. The method of claim 20, wherein each tile is labeled with a location that includes a coordinate set that is relative to the digital microscope slide that each tile originated from.

23. The method of claim 21, wherein the correlating the tile location of each tile received from the server includes correlating the coordinate set that each tile is labeled with to the coordinate system for the viewer interface.

24. The method of claim 23, wherein the coordinate set of each tile includes an x-axis coordinate and a y-axis coordinate.

25. The method of claim 23, wherein the coordinate system of the viewer interface includes an x-axis and a y-axis.

26. The method of claim 23, wherein the displaying of each tile that is provided by the server includes positioning each tile in the viewer interface based on each coordinate set that each tile is labeled with that is correlated to the coordinate system of the viewer interface.

27. The method of claim 20, wherein the receiving of each tile from the server includes receiving a plurality of lowest resolution tiles when the communications device receives an initial selection from the user to view the specimen, wherein the plurality of lowest resolution tiles includes each tile that depicts the specimen with a lowest magnification level of tiles stored by the server.

28. The method of claim 27, wherein the displaying each tile provided by the server includes displaying a substantially complete image of the specimen when displaying the plurality of lowest resolution tiles.

29. The method of claim 20, wherein the receiving each tile from the server includes receiving a plurality of higher resolution tiles from the server when the communications device receives the selection from the user to display the selected location of the specimen at the higher magnification that what is currently displayed by the viewer interface.

30. The method of claim 20, wherein the displaying each tile provided by the server includes displaying a less than complete image of the specimen when displaying the plurality of higher resolution tiles.

31. The method of claim 20, wherein the receiving each tile from the server prevents the communications device from occupying bandwidth of the communications device to divide each digital microscope image into the plurality of tiles.

32. The method of claim 20, wherein the receiving the selection from the user of the communications device includes the portion of the viewer interface that is touched by the user.

33. The method of claim 20, further comprising:
increasing a resolution of each tile displayed by the communications device after each tile has been received by the communications device from the server; and
decreasing the resolution of each tile displayed by the communications device after each tile has been received by the communications device from the server.

34. A viewing system for digital microscope slide images of a specimen provided by a server, comprising:
at least one processor; and
program code configured for execution by the at least one processor and configured to:
receive a single digital microscope slide image that captures the specimen at a high magnification level,
divide the single digital microscope slide image at the high magnification level into a plurality of tiles at a plurality of magnification levels by automatically adjusting the high magnification level of the single digital microscope slide image initially captured of the specimen to a plurality of magnification levels, with one or more of the magnification levels being at a lower magnification level than the initial high magnification level,
generate the plurality of tiles at the plurality of magnification levels from the single digital microscope slide image at the high magnification level initially captured of the specimen, wherein each of the tiles with one or more magnification levels being at a lower magnification level than the initial magnification level is derived from the single digital microscope slide image at the high magnification level,
store each tile derived from the single digital microscope slide image at the high magnification level in a tile storage system, wherein each tile is labeled with a magnification level of each tile and a location of each tile relative to the magnification level of each digital microscope image that each tile originated and correlates to a viewer interface of a communications device, and provide each tile from the tile storage system to the communications device that is labeled with a designated magnification level and a designated location as required by the communications device.

35. The viewing system of claim 34, wherein the program code configured for execution by the at least one processor is further configured to provide the location of the specimen relative to a coordinate system for the viewer interface.

36. The viewing system of claim 34, wherein each tile is labeled with a location that includes a coordinate set that is relative to the digital microscope slide that each tile originated from.

37. A viewing system for digital slide microscope slide images of a specimen by a communications device, comprising:
   at least one processor;
   program code configured for execution by the at least one processor and configured to:
      receive a selection from a user of the communications device that selects a location of the specimen relative to the viewer interface to be displayed at a selected magnification level by a viewer interface of the communications device,
      provide the selected magnification level and the location of the specimen relative to the viewer interface that is to be displayed at the selected magnification level to a server that stores a plurality of tiles that a plurality of digital microscope slide images that depict the specimen is divided into,
      receive each tile provided by the server that is labeled with the selected magnification level and a tile location that is associated with the selection of the user,
      correlate the tile location of each tile received from the server to a location of the viewer interface,
      display each tile provided by the server that is labeled with the selected magnification level and the tile location that is associated with the selection of the user based on the correlation of each tile location to each corresponding location of the viewer interface,
      receive an additional selection from the user that selects the location of the specimen relative to the viewer interface that is to be displayed at a higher magnification level than what is currently displayed by the viewer interface,
      display each tile that is labeled with the higher magnification selected by the user and the coordinate set that is adjacent to the location selected by the user,
      request from the server each tile at the higher magnification level that is adjacent to each tile currently displayed,
      store each tile at the higher magnification level that is adjacent to each tile currently displayed to display when the user pans through the specimen that is currently displayed by the viewer interface, and
      display an anticipated tile at the higher magnification level stored by the communications device when the user pans from a currently displayed tile to a location that is adjacent to the currently displayed tile without having to request the anticipated tile from the server after the user pans from the currently displayed tile.

38. A computer readable non-transitory storage medium encoded with a computer program, the program comprising instructions that when executed by one or more processors cause the one or more processors to perform operations, comprising:
   receiving a single digital microscope slide image that captures the specimen at a high magnification level;
   dividing the single digital microscope slide image at the high magnification level into a plurality of tiles at a plurality of magnification levels by automatically adjusting the high magnification level of the single digital microscope slide image initially captured of the specimen to the plurality of magnification levels, with one or more of the magnification levels being at a lower magnification level than the initial high magnification level;
   generating the plurality of tiles at the plurality of magnification levels from the single digital microscope slide image at the high magnification level initially captured of the specimen, wherein each of the tiles with one or more of the magnification levels being at a lower magnification level than the initial magnification level is derived from the single digital microscope slide image at the high magnification level;
   storing each tile derived from the single digital microscope slide image at the high magnification level in a tile storage system, wherein each tile is labeled with a magnification level of each tile and a location of each tile relative to the magnification level of each digital microscope slide image that each tile originated that correlates to a viewer interface of the communications device; and
   providing each tile from the tile storage system to the communications device that is labeled with a designated magnification level and a designated location as required by the communications device.

39. A computer readable non-transitory storage medium encoded with a computer program, the program comprising instructions that when executed by one or more processors cause the one or more processors to perform operations, comprising:
   receiving a selection from a user of a communications device that selects a location of the specimen relative to the viewer interface to be displayed at a selected magnification level by a viewer interface of the communications device;
   providing the selected magnification level and the location of the specimen relative to the viewer interface that is to be displayed at the selected magnification level to a server that stores a plurality of tiles that a plurality of digital microscope slide images that depict the specimen is divided into;
   receiving each tile that is provided by the server that is labeled with the selected magnification level and a tile location that is associated with the selection of the user;
   correlating the tile location of each tile received from the server to a location of the viewer interface;
   displaying each tile provided by the server that is labeled with the selected magnification level and the tile location that is associated with the selection of the user based on the correlation of each tile location to each corresponding location of the viewer interface;
   receiving an additional selection from the user that selects the location of the specimen relative to the viewer interface that is to be displayed at a higher magnification level than what is currently displayed by the viewer interface;
   display each tile that is labeled with the higher magnification selected by the user and the coordinate set that is adjacent to the location selected by the user;

request from the server each tile at the higher magnification level that is adjacent to each tile currently displayed;

store each tile at the higher magnification level that is adjacent to each tile currently displayed to display when the user pans through the specimen that is currently displayed by the viewer interface; and display an anticipated tile at the higher magnification level stored by the communications device when the user pans from a currently displayed tile to a location that is adjacent to the currently displayed tile without having to request the anticipated tile from the server after the user pans from the currently displayed tile.

* * * * *